(12) United States Patent
Belfadhel et al.

(10) Patent No.: US 7,696,388 B2
(45) Date of Patent: Apr. 13, 2010

(54) PROCESS FOR PRODUCING BISPHENOL-A

(75) Inventors: Hatem Abdallah Belfadhel, Roosendaal (NL); Umesh Krishna Hasyagar, Karnataka (IN); Gurram Kishan, Karnataka (IN); Rathinam Jothi Mahalingam, Karnataka (IN)

(73) Assignee: SABIC Innovative Plastics IP B.V., Bergen op Zoom (NL)

( * ) Notice: Subject to any disclaimer, the term of this patent is extended or adjusted under 35 U.S.C. 154(b) by 0 days.

(21) Appl. No.: 11/962,642

(22) Filed: Jul. 9, 2008

(65) Prior Publication Data

US 2010/0010273 A1      Jan. 14, 2010

(51) Int. Cl.
    *C07C 39/16* (2006.01)
(52) U.S. Cl. .................................... 568/723
(58) Field of Classification Search .................. 568/723
    See application file for complete search history.

(56) References Cited

U.S. PATENT DOCUMENTS

| | | | |
|---|---|---|---|
| 4,107,218 A | 8/1978 | Konrad et al. | |
| 4,209,646 A | 6/1980 | Gac et al. | |
| 4,354,046 A | 10/1982 | Ladewig et al. | |
| 4,590,303 A * | 5/1986 | Mendiratta | 568/728 |
| 4,766,254 A | 8/1988 | Faler et al. | |
| 4,822,923 A | 4/1989 | Li | |
| 4,942,265 A | 7/1990 | Iimuro et al. | |
| 4,954,661 A | 9/1990 | Iimuro et al. | |
| 5,288,926 A | 2/1994 | Patrascu et al. | |
| 5,300,702 A | 4/1994 | Perkins et al. | |
| 6,197,916 B1 * | 3/2001 | Pressman et al. | 528/110 |
| 6,303,835 B1 * | 10/2001 | Shafer et al. | 568/806 |
| 2004/0181100 A1 * | 9/2004 | Lundquist | 568/723 |
| 2006/0069292 A1 | 3/2006 | Kumar et al. | |

FOREIGN PATENT DOCUMENTS

| | | |
|---|---|---|
| DE | 2642596 A1 | 4/1977 |
| EP | 1149816 A1 | 10/2001 |
| GB | 1565667 | 4/1980 |
| WO | 0222531 A1 | 3/2002 |
| WO | 2006039088 A1 | 4/2006 |

OTHER PUBLICATIONS

Terasaki et al., 39 Environ. Sci. Technol., 3703-07 (2005).*
Singh, A.P.; "Preparation of Bisphenol-A Over Zeolite Catalysts"; Catalysis Division, National Chemical Laboratory, Pune 411 008, India; Recieved: Jun. 18, 1992; Accepted: Sep. 23, 1992; Document No. XP-001105404; 12 Pages (1992).
International Search Report; International Application No. PCT/IB2008/055393; International Filing Date: Dec. 17, 2008; Date of Mailing: Apr. 8, 2009; 7 pages.
Written Opinion of the International Searching Authority: International Application No. PCT/IB2008/055393; International Filing Date: Dec. 17, 2008; Date of Mailing: Apr. 8, 2009; 9 Pages.

* cited by examiner

*Primary Examiner*—Brian J Davis (57) ABSTRACT

A process for preparing 2,2-bis(4-hydroxyphenyl)propane (p,p-bisphenol-A) from 2,4,4-trimethyl-2-(4-hydroxyphenyl)chroman (chroman 1.5) is disclosed. Phenol and chroman 1.5 are contacted over an acidic ion exchange resin at a given temperature for a given period of time. The process results in improved quality of p,p-bisphenol-A, better performance of catalyst, improved raw material usage, and reduced waste.

21 Claims, 11 Drawing Sheets

PROCESS FOR PRODUCING BISPHENOL-A

BACKGROUND

The present disclosure relates generally to processes for forming bisphenol-A, such as processes for purifying waste streams resulting from the synthesis of 2,2-bis(4-hydroxyphenyl)propane, also known as bisphenol-A, BPA, para, para-BPA, or p,p-BPA. For example, one embodiment of the disclosure relates to methods for producing bisphenol-A from an impurity, such as chroman 1.5. Also included are various isolated, converted, or purified products formed by these processes.

Bisphenol-A is used as an intermediate in the production of certain polycarbonates, epoxies, phenoxies, polysulfones, and polyester resins. Bisphenol-A itself is commercially produced by the condensation of phenol with acetone in the presence of an acid catalyst and in the presence of a cocatalyst (e.g., a mercaptan) which acts as a reaction rate accelerator. A common method involves the use of a sulfonated cation exchange resin in the free acid form, through which the phenol and acetone mixture is run. The resulting product stream can then be purified to obtain bisphenol-A and a mother liquor containing various byproducts and impurities. The mother liquor is distilled to reduce water. Fresh phenol, acetone, and co-catalyst are then added to the mother liquor and fed to the sulfonated cation exchange resin again.

One of these impurities in the mother liquor is chroman 1.5, also known as 4-(2,4,4-trimethyl-chroman-2-yl)-phenol or 2,4,4-trimethyl-2-(4-hydroxyphenyl)chroman. Depending on conditions, chroman 1.5 can be produced at 0.8 to 1.5 weight percent concentrations. Chroman 1.5 has the chemical structure shown below:

Chroman 1.5

The mother liquor may be further processed to increase the overall yield of the reaction. For example, the mother liquor may be sent to a tar cracker unit to crack the impurities into phenol and other light or heavy molecules. The phenol can then be separated from the heavy molecules (via distillation) and recycled into the bisphenol-A production line. The light molecules remain with the phenol and are also recycled into the bisphenol-A production line.

However, chroman 1.5 co-distills with phenol and is thus difficult to remove via distillation. Although present in low quantities of from 0.1 to 6 weight percent in the phenol, the presence of chroman 1.5 has been found to reduce the lifetime and the selectivity of the acid catalyst used in the phenol-acetone condensation process. In addition, chroman 1.5 has color-forming tendencies at elevated temperatures and its presence is unsuitable in the polycarbonates made from the bisphenol-A, which may need to be transparent and clear.

It would be desirable to remove or convert impurities, such as chroman 1.5, to improve the performance of the acid catalyst system, increase catalyst lifetime, improve the quality of the resulting bisphenol-A, and/or increase the yield by improving the usage of the raw material (i.e. minimizing the amount of waste that needs to be disposed).

BRIEF DESCRIPTION

Disclosed, in various embodiments, are methods for producing bisphenol-A, purifying a bisphenol-A waste stream or purge stream, and/or converting an impurity to bisphenol-A. Also included are various isolated, converted, or purified products formed by these methods.

In embodiments, a process for producing 2,2-bis(4-hydroxyphenyl)propane (p,p-BPA) comprises:
providing a liquid stream comprising phenol and 2,4,4-trimethyl-2-(4-hydroxyphenyl)chroman (chroman 1.5); and
feeding the liquid stream to an acidic ion exchange resin at a temperature of from about 45° C. to about 100° C. to produce an effluent stream containing p,p-BPA, the acidic ion exchange resin having greater than 2%, including greater than 4% crosslinkage, and preferably less than about 20% crosslinkage.

The chroman 1.5 may comprise from about 0.1 weight percent to about 6 weight percent of the liquid stream.

In some embodiments, the liquid stream may further comprise a mercaptan selected from the group consisting of 3-mercaptopropionic acid, an ethene thiol, a propane thiol, an aliphatic thiol, and an aromatic thiol.

In other embodiments, the acidic ion exchange resin may have from 6% to 10% crosslinkage.

In further embodiments, the acidic ion exchange resin may be a resin selected from the group consisting of sulfonated styrenedivinylbenzene resins, sulfonated styrene resins, phenol formaldehyde sulfonic acid resins, and benzene formaldehyde sulfonic acid resins.

Moreover, the ion exchange resin may contain sulfonic acid groups.

In still other embodiments, the temperature may be from about 53° C. to about 93° C. The temperature may be from about 80° C. to about 95° C.

The weight hourly space velocity WHSV of the liquid stream in the ion exchange resin may be from 0 to about 20 hr$^{-1}$. In other embodiments, the WHSV may be from about 0.5 to about 5 hr$^{-1}$.

The effluent stream may comprise from about 1 weight percent to about 12 weight percent of p,p-PBA.

In further embodiments, a process for converting 2,4,4-trimethyl-2-(4-hydroxyphenyl)chroman (chroman 1.5) into 2,2-bis(4-hydroxyphenyl)propane (p,p-BPA) comprises:
providing a liquid stream comprising phenol and chroman 1.5; and
feeding the liquid stream to an acidic ion exchange resin at a temperature of from about 45° C. to about 100° C. to convert at least 50 weight percent of the chroman 1.5 to p,p-BPA.

The acidic ion exchange resin may have greater than 2% crosslinkage or have 8% crosslinkage.

At least 70 weight percent or at least 90 weight percent of the chroman 1.5 may be converted to p,p-BPA.

In further embodiments, a process for converting 2,4,4-trimethyl-2-(4-hydroxyphenyl)chroman (chroman 1.5) into 2,2-bis(4-hydroxyphenyl)propane (p,p-BPA) comprises:
providing a liquid stream consisting essentially of phenol and chroman 1.5; and
exposing the liquid stream to an acidic ion exchange resin at a temperature of from about 45° C. to about 100° C. to convert the chroman 1.5 to p,p-BPA;

wherein the weight hourly space velocity WHSV of the liquid stream in the acidic ion exchange resin is from 0 to about 20 hr$^{-1}$.

The temperature may be from about 80° C. to about 100° C.

The acidic ion exchange resin may have greater than 4% crosslinkage.

At least 90 weight percent of the chroman 1.5 may be converted to p,p-BPA at a WHSV less than 6 at a temperature greater than 80° C.

In additional embodiments, a method for improving the lifetime of an ion exchange resin catalyst in the production of 2,2-bis(4-hydroxyphenyl)propane (p,p-BPA) is disclosed, comprising:

reacting acetone and phenol in a reactor in the presence of an ion exchange resin catalyst to form a reactor product stream comprising p,p-BPA, and 2,4,4-trimethyl-2-(4-hydroxyphenyl)chroman (chroman 1.5), and phenol;

separating the reactor product stream into a first product stream containing p,p-BPA and a byproduct stream;

recycling a first fraction x of the byproduct stream to the reactor;

treating the remainder of the byproduct stream with a cracking catalyst to convert the byproduct stream into a phenol-containing stream;

treating a second fraction y of the phenol-containing stream with an acidic ion exchange resin to reduce the amount of chroman 1.5 in the phenol-containing stream; and recycling the treated second fraction to the reactor;

wherein the acidic ion exchange resin has 2% or greater crosslinkage.

The lifetime of the ion exchange resin catalyst may be increased by a factor of between 1.5 and 3, or greater than 3, compared to simply recycling the phenol-containing stream to the reactor without treating it using the acidic ion exchange resin.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The processes of the present disclosure comprise reducing the amount of chroman 1.5 by converting it to p,p-BPA in the presence of phenol. This can be accomplished by taking a liquid stream comprising phenol and chroman 1.5 and passing it through an acidic ion exchange resin at a temperature of from about 45° C. to about 100° C. An acidic ion exchange resin is also known as a cation exchange resin. The chroman 1.5 reacts with the phenol in the acidic ion exchange resin to form p,p-BPA. The amount of p,p-BPA formed is determined by the concentration of the chroman 1.5 in the liquid stream.

The acidic ion exchange resins of the present disclosure are generally made from copolymers of styrene and divinylbenzene and generally contain sulfonic acid groups. Other exemplary acidic ion exchange resins include those made from sulfonated styrenedivinylbenzene resins, sulfonated styrene resins, phenol formaldehyde sulfonic acid resins, and benzene formaldehyde sulfonic acid resins.

The copolymers used to make the acidic ion exchange resin may be crosslinked together. The degree of crosslinkage (CL) is generally measured by percentage. In embodiments, the acidic ion exchange resin has greater than 4% crosslinkage. In more specific embodiments, the acidic ion exchange resin has 8% crosslinkage. In other embodiments, the acidic ion exchange resin contains from about 6% to about 10% crosslinkage. In embodiments, the acidic ion exchange resin contains from greater than 4% to about 20% crosslinkage. In further embodiments, the crosslinkage is 20% or less.

A suitable resin is T-66 resin available from Thermax. Other exemplary resins include K1131, K1221, and K1431 resins available from Lanxess. Other resins are also available from Purolite, Dow, and Rohm & Haas.

The acidic ion exchange resin may be in a fixed or fluidized bed mode. The liquid stream can be contacted with the acidic ion exchange resin in either a batch mode or a continuous mode. For example, a stirring fixed bed in a continuous stirred tank reactor may be used. In specific embodiments, the temperature may be from about 53° C. to about 93° C. In other specific embodiments, the temperature may be from about 80° C. to about 95° C. Generally, the feed line to the ion exchange resin is maintained within this temperature range. The ion exchange resin is also maintained within this temperature range.

The residence time of the liquid stream in the ion exchange resin depends on the WHSV and the temperature. The residence time may be from about 0.5 hour to about 5 hours. In more specific embodiments, the residence time is from 0.6 hour to about 1 hour. The weight hourly space velocity WHSV may be 0 in a batch reaction and go up to about 40 $hr^{-1}$. In other embodiments, the WHSV is from 0.5 $hr^{-1}$ to about 20 $hr^{-1}$ or from about 0.5 $hr^{-1}$ to about 5 $hr^{-1}$. In still other embodiments, the WHSV is 10 $hr^{-1}$ or less, 5 $hr^{-1}$ or less, or 1 $hr^{-1}$ or less. When the WHSV is 5 $hr^{-1}$ or less, p,p-BPA is generally favored over its isomer o,p-BPA.

The temperature can affect the amount by which the chroman 1.5 is reduced. At a temperature of 53° C., about 25% of the chroman 1.5 is reduced. At a temperature of 85° C., the reduction is greater than 99.85%.

In specific examples, treating a liquid stream at a temperature between 80° C. and 95° C. with a cationic (i.e., acidic) ion exchange resin having 8% crosslinkage at a WHSV of 10 $hr^{-1}$ would allow for more than 70% removal of chroman 1.5. At a WHSV of less than 5 $hr^{-1}$, more than 90% of the chroman 1.5 would be removed.

Figure 1:
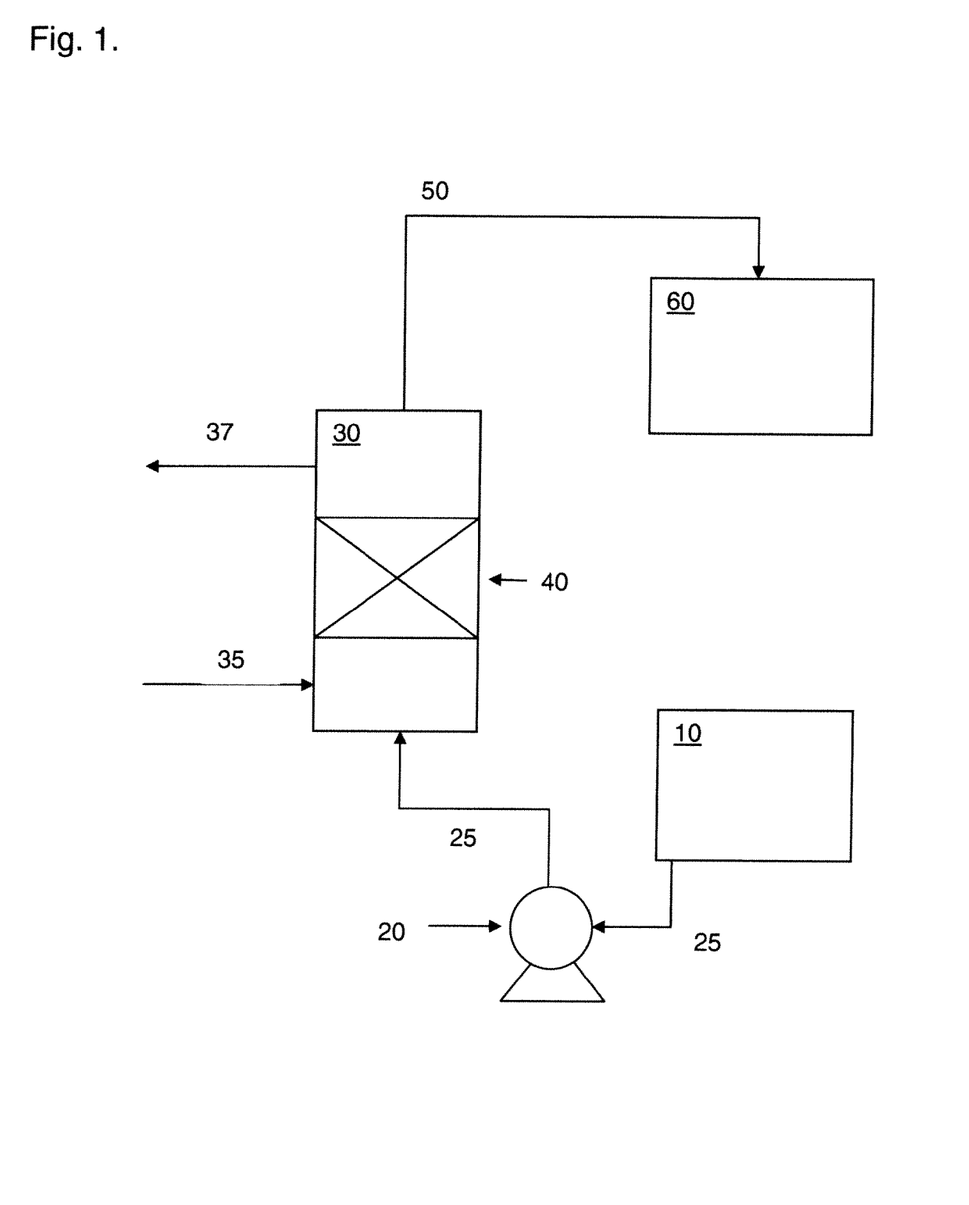
FIG. 1 is a first embodiment of a continuous reactor system for practicing the methods of the present disclosure.

FIG. 1 is one embodiment of a continuous reactor system for practicing the methods of the present disclosure. A feed tank 10 contains liquid comprising phenol and chroman 1.5. A liquid stream is pumped from the feed tank 10 by a pump 20 through feed line 25 and fed to a reactor 30 containing an acidic ion exchange resin 40. The effluent exits the reactor 30 through product line 50. The effluent contains a reduced amount of chroman 1.5 and an increased amount of p,p-BPA. The effluent is then collected in product tank 60. The feed line 25 and product line 50 may be insulated to maintain a constant temperature. The reactor temperature may also be maintained by circulating thermal liquid which enters via incoming stream 35 and exits via outgoing stream 37. In smaller reactors, the heating of the reactor may be done by electrical tracing.

Figure 2:
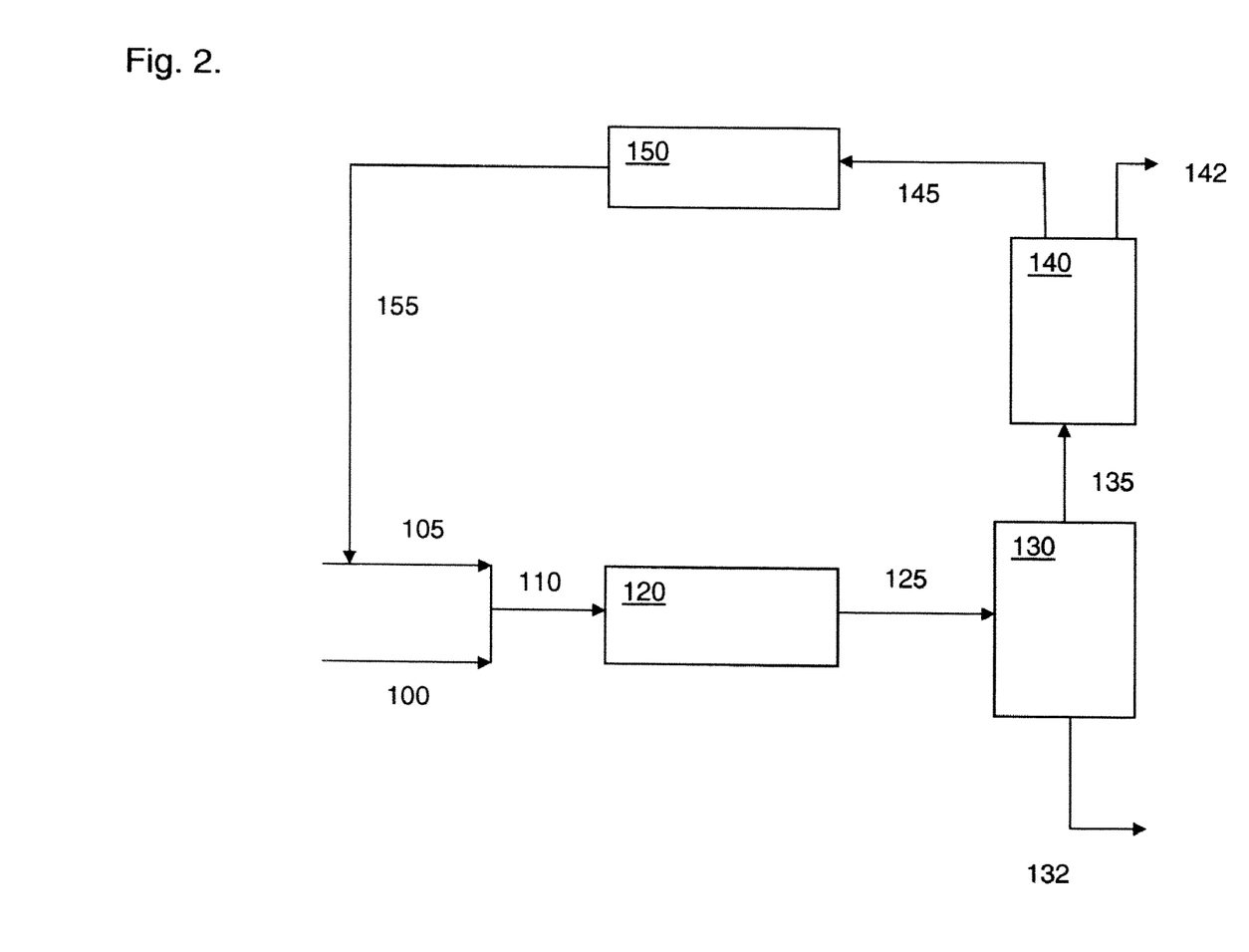
FIG. 2 is a second embodiment of a continuous system for using the methods of the present disclosure.

FIG. 2 is a second embodiment of a continuous system for using the methods of the present disclosure. Acetone 100 and phenol 105 are mixed into a reactant stream. The reactant stream may comprise other components as well, such as mercaptan reaction rate accelerator. The reactant stream is fed through feed line 110 into a reactor 120 to produce a product stream containing p,p-BPA and other byproducts. The product stream exits reactor 120 via reactor product line 125 and enters separator 130, wherein the p,p-BPA is separated from the product stream (represented by numeral 132). For example, the separator may be a distillation column, evaporator, or crystallizer. The mother liquor is the remainder of the product stream. The mother liquor exits the separator 130 via separator product line 135 and enters tar cracker 140, which decomposes some of the byproducts into useful reactants (such as phenol, residual p,p-BPA, o,p-BPA, and chroman 1.5) and heavies. The heavies are separated from the useful reactants and the heavies exit the system via waste line 142. A liquid stream comprises the useful reactants from the tar cracker 140 and comprises phenol and chroman 1.5. The liquid stream exits tar cracker 140 via exit line 145 and enters the acidic ion exchange resin 150. In the resin 150, the chroman 1.5 is converted into p,p-BPA so that the amount of chroman 1.5 is reduced and the amount of p,p-BPA is increased. The liquid stream then exits the resin 150 via product line 155 and can be recycled through the continuous reactor system again.

As a result of the processes of the present disclosure, 1 mole of chroman 1.5 and 2 moles of phenol are converted into 2 moles of p,p-BPA.

Figure 3:
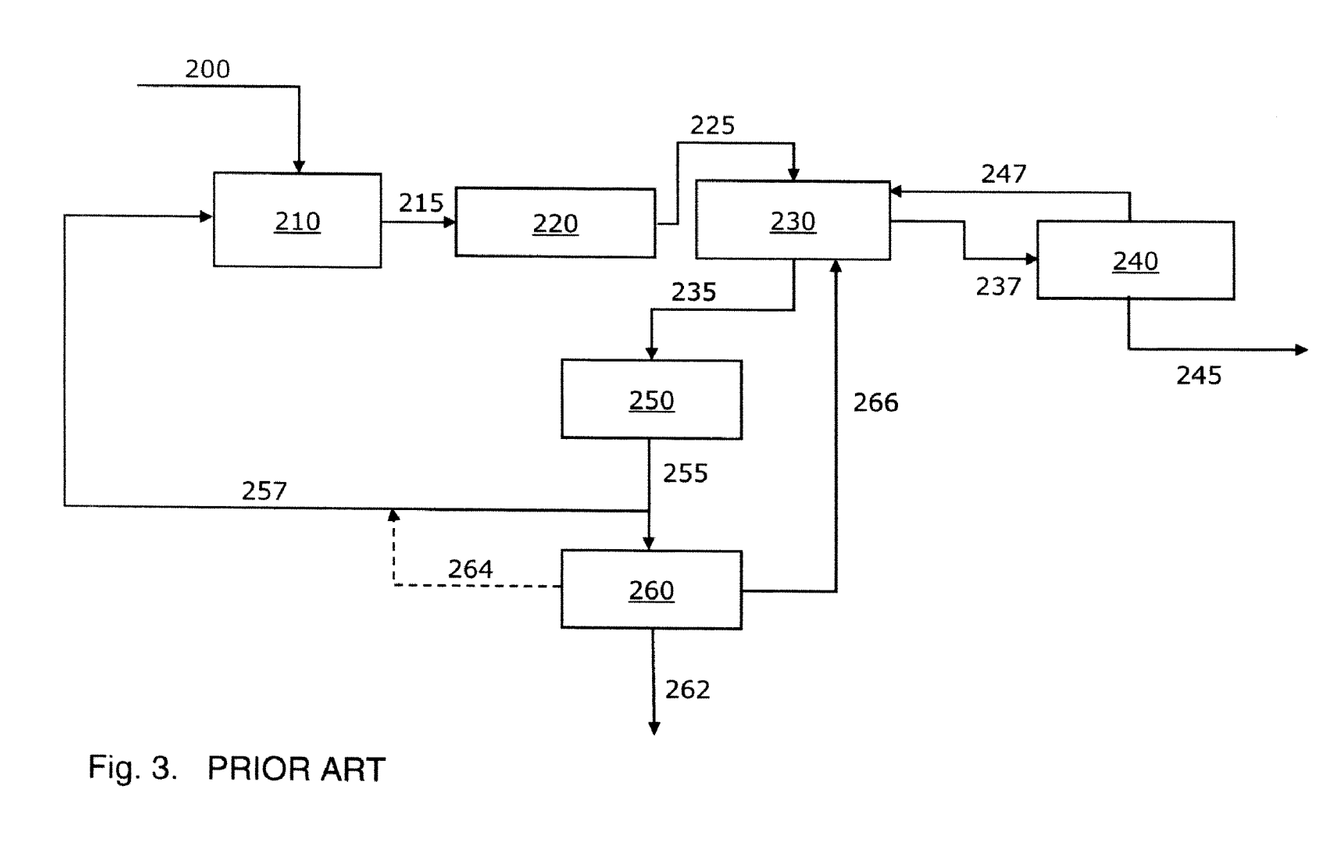
FIG. 3 is a prior art embodiment of a process that allows chroman 1.5 to build up during the manufacture of p,p-BPA.

FIG. 3 is a prior art embodiment of a process that allows chroman 1.5 to build up during the manufacture of p,p-BPA. Fresh phenol, acetone, and co-catalyst are fed via feed line 200 into reactor 210. Reactor 210 contains the sulfonated cation exchange resin that produces p,p-BPA. The BPA reactor effluent 215 is fed to crystallizer 220. The crystallizer effluent 225 is fed to separator 230, which separates the effluent 225 into wet mother liquor 235 and a BPA-phenol adduct stream 237. The BPA-phenol adduct stream 237 is fed to a purifier 240 to obtain the BPA 245 and the phenol 247. The phenol stream 247 is fed back to separator 230. The wet mother liquor 235 goes to a dehydrator 250 to reduce the amount of water. Dry mother liquor 255 exits the dehydrator 250. Some of the dry mother liquor 255 is purged to the tar cracker 260 and some of the dry mother liquor 255 is recycled to the reactor 210 via recycle line 257. In the tar cracker 260, the mother liquor 255 is cracked into tar and a liquid stream. The liquid stream contains tar cracking phenol and chroman 1.5. The tar is disposed of via disposal line 262. The liquid stream may be recycled back to the reactor 210 via recycle line 264 or back to the separator 230 via recycle line 266.

Figure 4:
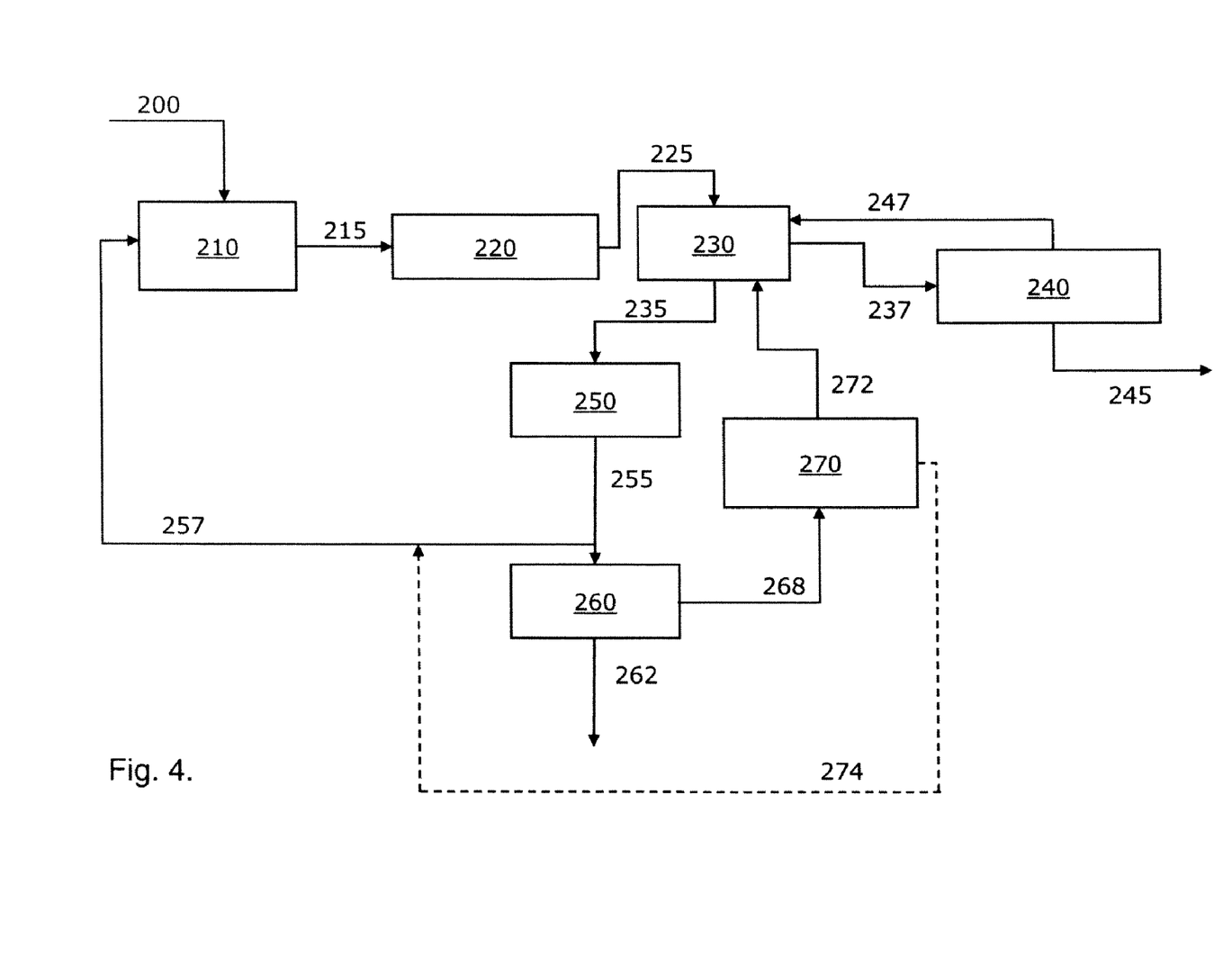
FIG. 4 is an embodiment of a process that removes chroman 1.5 from a phenol stream.

FIG. 4 is an embodiment of a process that removes chroman 1.5 from a phenol stream. Rather than feeding the liquid stream into recycle lines 264 or 266 as in FIG. 3, the liquid stream is fed via effluent line 268 into an acidic ion exchange resin 270. In the resin, the chroman 1.5 is converted into p,p-BPA to reduce the amount of chroman 1.5 and increase the amount of p,p-BPA in the liquid stream. The liquid stream is then recycled back to the separator 230, where the p,p-BPA can be removed (via BPA-phenol adduct stream 237) or fed back into recycle line 257 via recycle line 274.

The following examples are provided to illustrate the methods of the present disclosure. The examples are merely illustrative and are not intended to limit devices made in accordance with the disclosure to the materials, conditions, or process parameters set forth therein.

EXAMPLES

Example 1

A reactor system was set up as shown in FIG. 1. The ion exchange resin was T-66 resin, obtained from Thermax, having 8% crosslinkage. The feed and product lines were thermally insulated and maintained at a constant temperature of 60° C. Samples were collected at regular intervals and analyzed by HPLC.

The HPLC analysis was performed using acetophenone and anisole as an internal standard on a $C_{18}$ column with UV detector.

Effect of Temperature:

Two reactions were carried out with the reactor, one at a temperature of 53° C. and another at a temperature of 85° C. A phenol stream containing 1.99 weight percent of chroman 1.5 was passed through the reactor bed. The operating conditions maintained were WHSV of 1 $hr^{-1}$ and a residence time of 1.0 hr.

At 53° C., the chroman 1.5 in the resulting effluent was measured and found to be less than 1.5%. This result showed that treatment with an acidic ion exchange resin at 53° C. reduced the amount of chroman 1.5 in the phenol by 25%.

At 85° C., the amount of chroman 1.5 in the resulting effluent was reduced by more than 99.85%. In addition, ~2 weight percent of p,p-BPA was found in the effluent.

Effect of WHSV:

The reactor bed was maintained at 85° C. A phenol stream containing 1.99 weight percent of chroman 1.5 was passed through the reactor bed. The WHSV was varied from 1 to 5.05 $hr^{-1}$.

Figure 5:
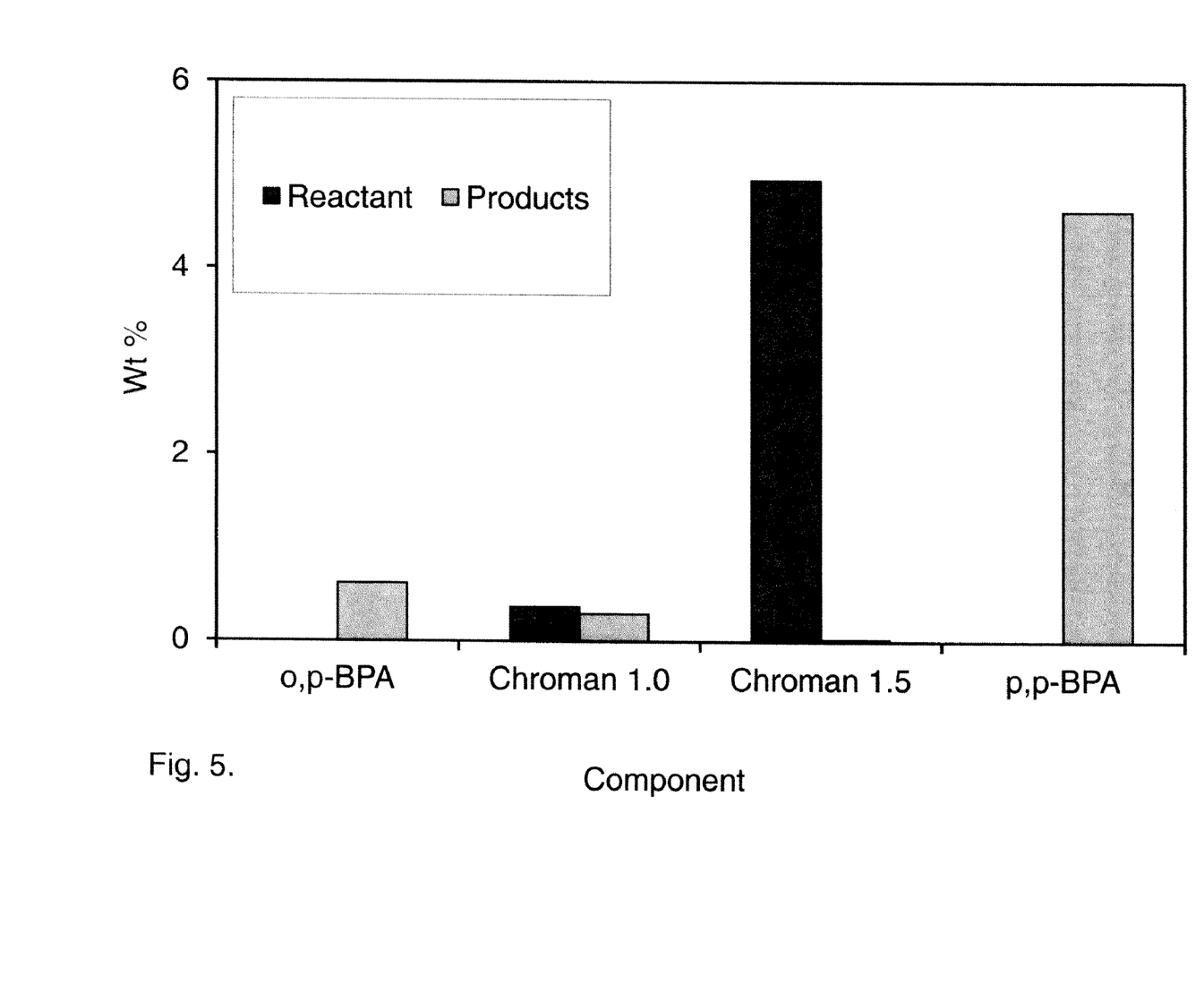
FIG. 5 is a graph showing the relative amounts of various reactants and products in a batch reaction according to the methods of the present disclosure.

Batch Process:

Batch reactions were also carried out. The reaction progressed very slowly at 85° C. with mild stirring. However, at 93° C. and residence time of 4 hrs, greater than 99% reduction of chroman 1.5 was achieved. FIG. 5 is a graph showing the relative amounts of the various reactants and products in this batch reaction. The initial concentration of initial concentration of chroman 1.5 was 4.95 weight percent; the final concentration of p,p-BPA was 4.6 weight percent.

Similar reactions were carried out with fresh phenol and 4.95 weight percent of chroman 1.5 for 4 hrs. HPLC of the product showed 4.6 weight percent of p,p-BPA and 0.025 weight percent of chroman 1.5. Thus, conversion of chroman 1.5 to p,p-BPA was achieved.

Figure 6:
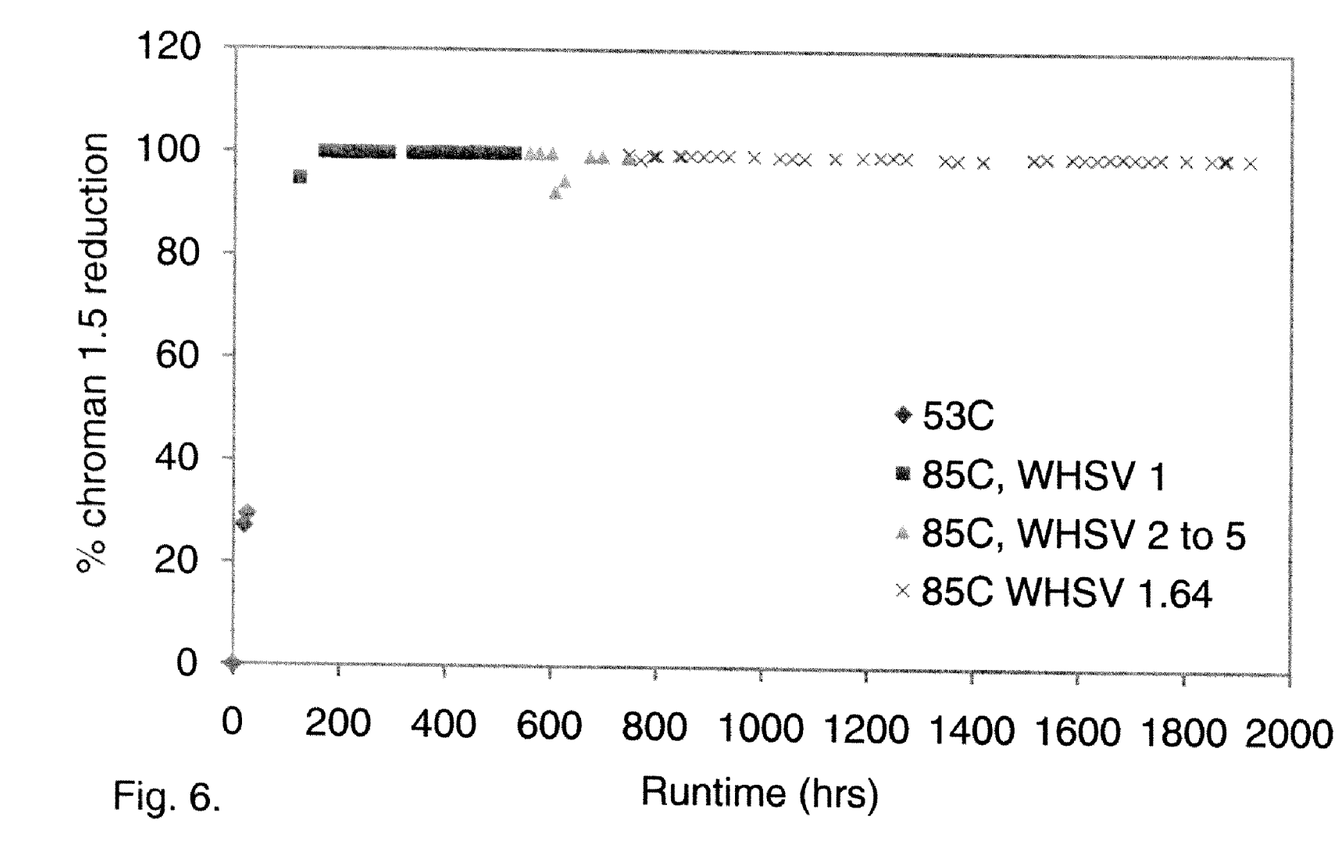
FIG. 6 is a graph showing the percentage of chroman 1.5 as a function of time as the temperatures and WHSV are varied over the runtime of a particular batch.

FIG. 6 is a graph showing the percentage of chroman 1.5 as a function of time as the temperatures and WHSV were varied over the runtime of a particular batch. The temperature was changed from 53° C. to 85° C. The WHSV was held at 1, then varied from 2 to 5, then held at 1.64.

Figure 7:
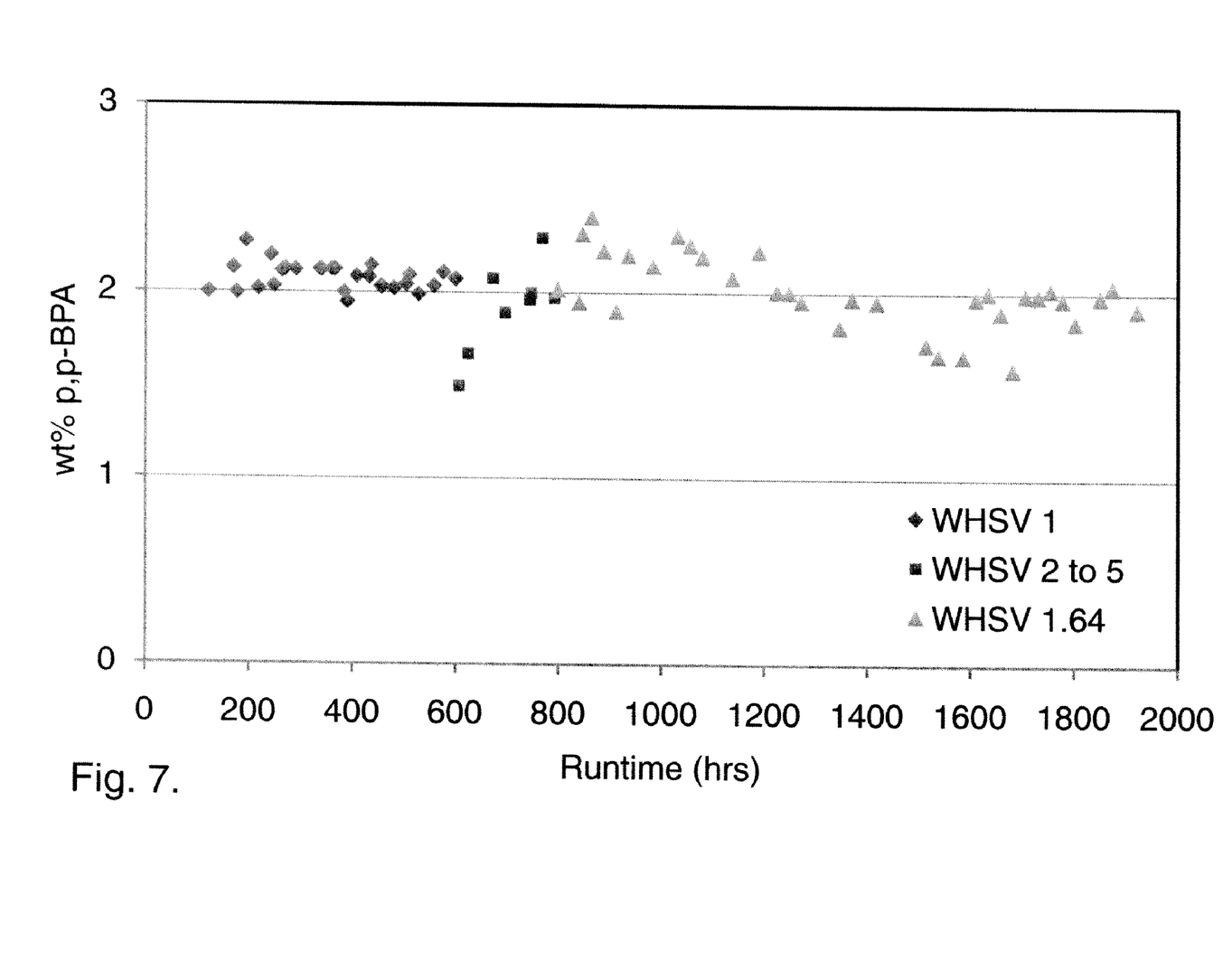
FIG. 7 is a graph showing the weight percentage of p,p-BPA formation as a function of time as the temperatures and WHSV are varied over the runtime of the same batch as FIG. 6.

FIG. 7 is a graph showing the weight percentage of p,p-BPA formation as a function of time as the temperatures and WHSV were varied over the runtime of the same batch as FIG. 6. This shows that p,p-BPA formation is occurring concurrently with chroman 1.5 reduction. Here, all of the datapoints were measured at 85° C.; no data was measured at 53° C.

Figure 8:
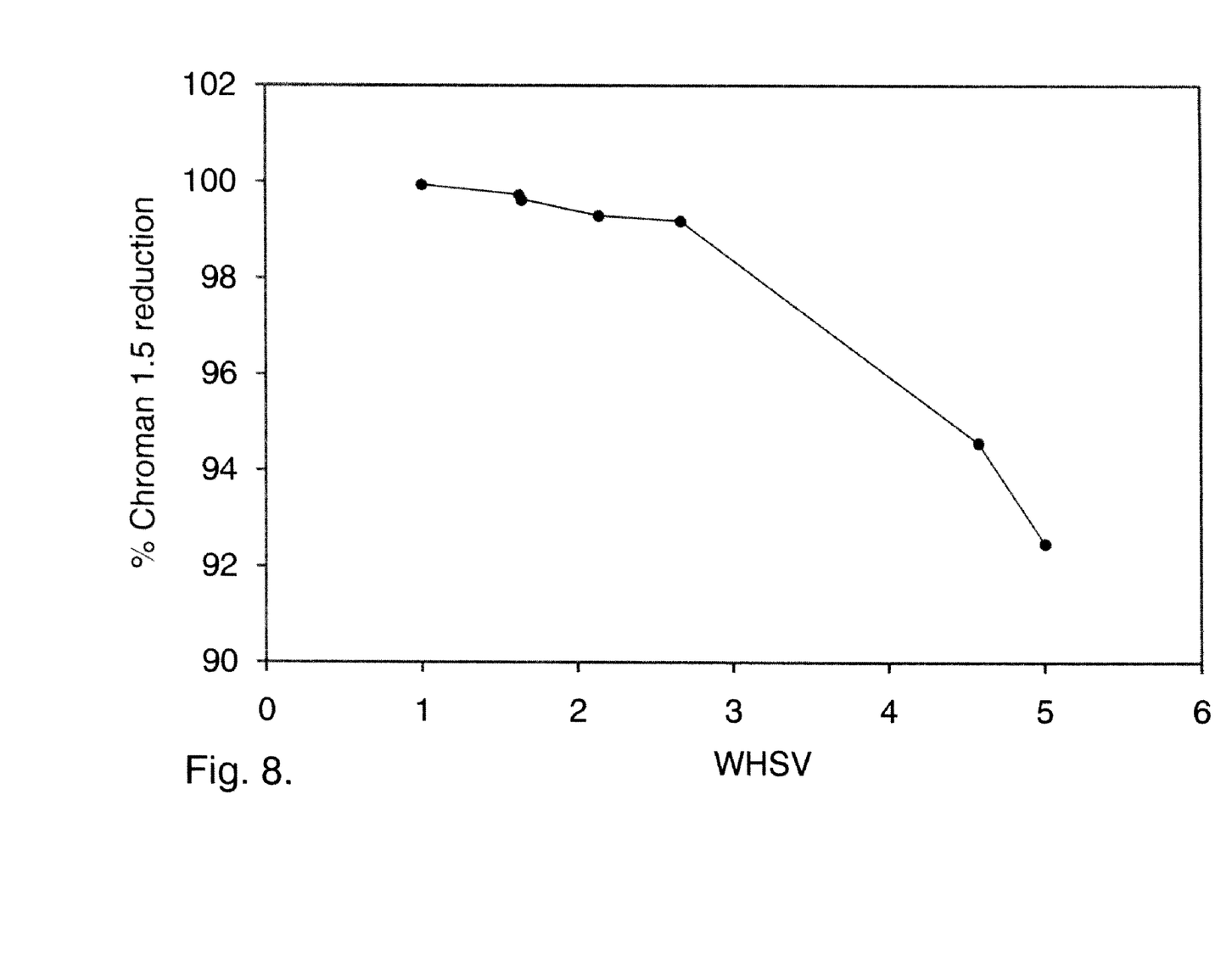
FIG. 8 is a graph showing the percentage of chroman 1.5 as a function of WHSV at 83° C.

FIG. 8 is a graph showing the percentage of chroman 1.5 as a function of WHSV at 83° C. The reduction of chroman 1.5 is optimum around 1.66 WHSV in these conditions.

Figure 9:
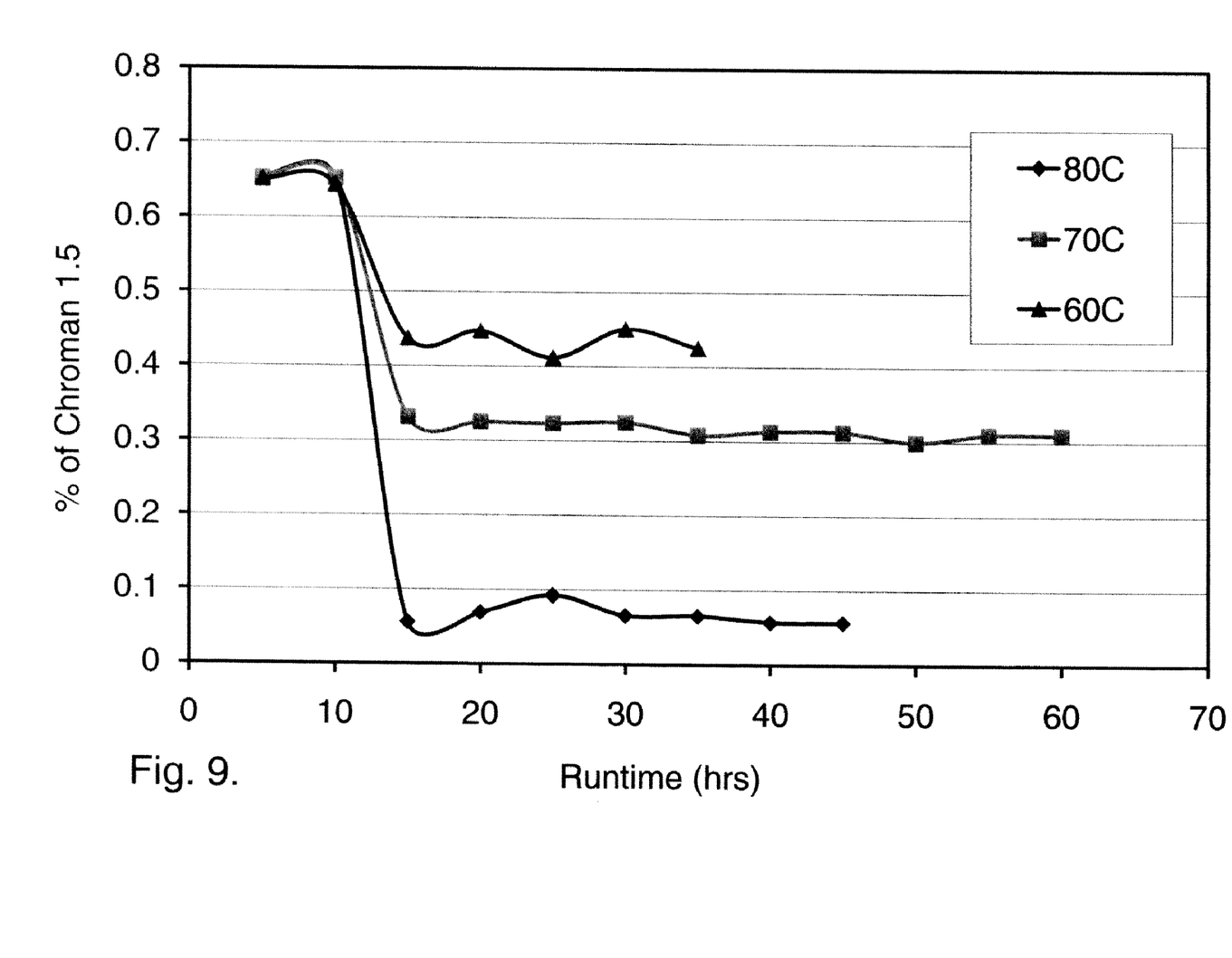
FIG. 9 is a graph showing the percentage of chroman 1.5 remaining in the effluent after being run through a Thermax T-66 resin @ 1.0 WHSV at 60° C., 70° C., or 80° C.

Additional experiments were also run. FIG. 9 is a graph showing the percentage of chroman 1.5 remaining in the effluent after being run through a Thermax T-66 resin @ 1.0 WHSV at 60° C., 70° C., or 80° C. as a function of time. It is clear that chroman 1.5 is reduced better at higher temperatures.

Example 2

An experiment was run in a continuous system similar to that of FIG. 2, where p,p-BPA was produced, the mother liquor was run through an acidic ion exchange resin (T-66), and then recycled. The total p,p-BPA production was monitored to examine the effect of the purification process, as well as the amount of deactivation of the catalyst used to make the p,p-BPA.

The temperature was 85° C. and the WHSV was 1. The experiment was run over a period of about 500 hours and the amount of impurities was measured.

Again, the reduction in chroman 1.5 occurred very quickly and was maintained. The reduction was close to 100%.

p,p-BPA formation occurred fairly quickly. The p,p-BPA concentration in the feed was 0.034 weight percent, but near 2 weight percent in the effluent. To ensure the p,p-BPA was formed from chroman 1.5 conversion, the acetone concentration was also measured. The feed and effluent had the same amount of acetone, indicating that the additional p,p-BPA came from chroman 1.5 conversion rather than reaction of acetone with phenol. The o,p-BPA concentration in the feed was 0.096 weight percent, but was about 0.25 weight percent in the effluent. This indicated that o,p-BPA was being formed from chroman 1.5 reduction as well.

Figure 10:
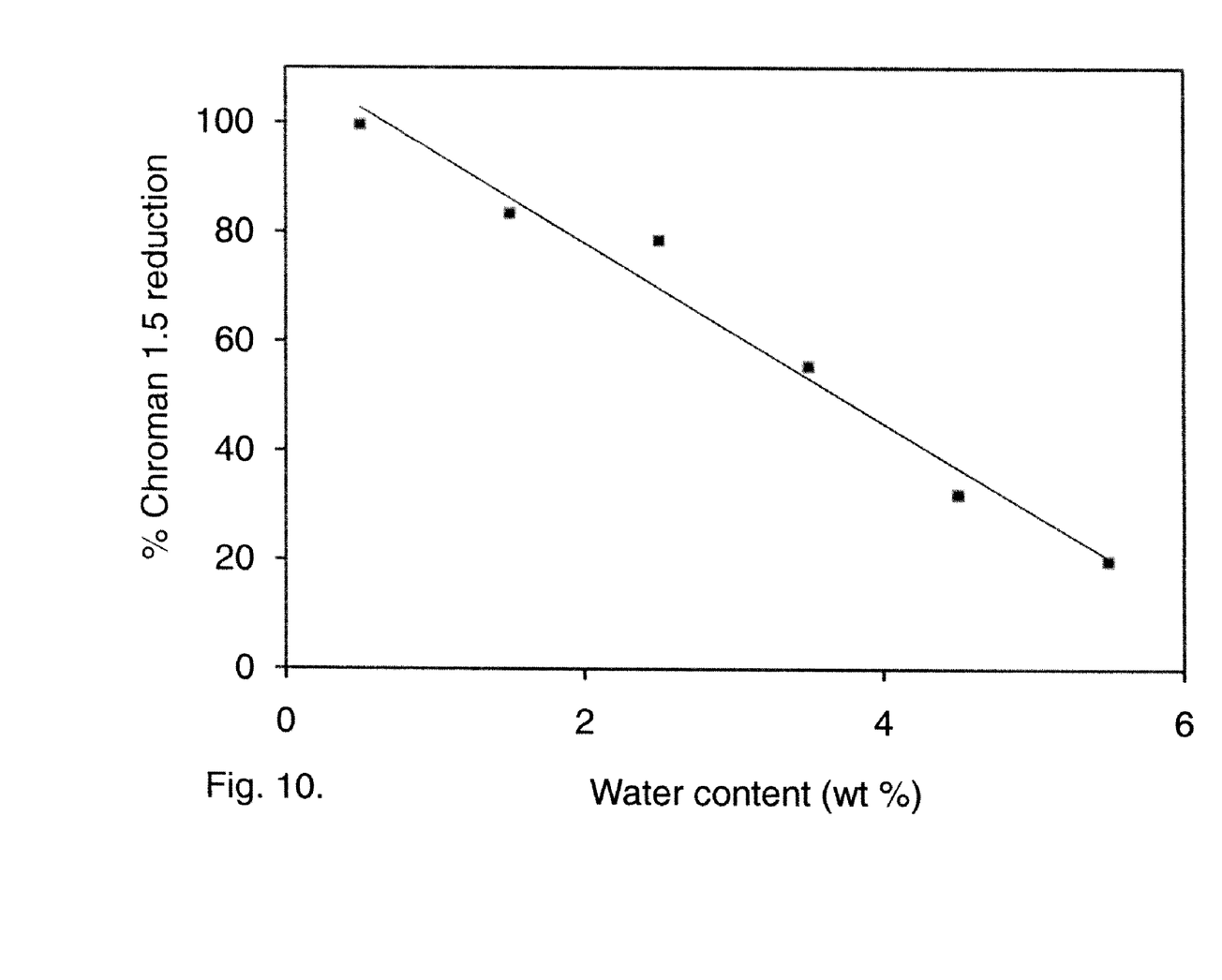
FIG. 10 is a graph showing the effect of water content on the reduction in chroman 1.5.

FIG. 10 is a graph showing the effect of water content on the reduction of chroman 1.5. As the water content increased, the reduction in chroman 1.5 decreased.

Example 3

The effect of the degree of crosslinkage of the acidic ion exchange resin on the conversion of chroman 1.5 to p,p-BPA was determined. Four different resins containing 2%, 4%, 8%, and 20% crosslinkage were used. The 2% resin was A121 from Rohm & Haas. The 4% resin was A131 from Rohm & Haas. The 8% resin was T-66 from Thermax. The 20% resin was T-63 from Thermax. They were exposed to a feed in a batch reaction at 93° C. for four hours with mild stirring. The results obtained are shown in Table 1 below.

TABLE 1

| Component | Unit | Amt in Feed | Amt from 2% resin | Amt from 4% resin | Amt from 8% resin | Amt from 20% resin |
|---|---|---|---|---|---|---|
| chroman 1.5 | weight percent | 2.48925 | 1.4122 | 1.29875 | 0.0148 | 0.639 |
| p,p-BPA | weight percent | 0 | 0.9069 | 1.1734 | 2.63315 | 1.5538 |
| chroman 1.5 reduction | % | | 43.3 | 47.8 | 99.4 | 74.3 |

The resins having 8% and 20% crosslinkage performed best. The performance of the resin appeared to peak at 8% crosslinkage.

Example 4

The effect of WHSV on the conversion of chroman 1.5 to p,p-BPA was determined. Four WHSVs were tested: 10 $hr^{-1}$, 5 $hr^{-1}$, 3.3 $hr^{-1}$, and 2.5 $hr^{-1}$ at 93° C. Results are shown in Table 2. The units are given in grams feed/grams catalyst/hr.

TABLE 2

|  | Feed | 10 | 5 | 3.3 | 2.5 |
|---|---|---|---|---|---|
| Chroman 1.5 (%) | 1.49 | 0.31 | 0.04 | 0.01 | 0.00 |
| p,p-BPA (%) | 0.03 | 1.32 | 1.89 | 2.07 | 2.16 |
| o,p-BPA (%) | 0.08 | 0.67 | 0.51 | 0.35 | 0.33 |
| Chroman 1.0 (%) | 0.12 | 0.75 | 0.76 | 0.74 | 0.74 |

As the WHSV decreased, the conversion of chroman 1.5 to p,p-BPA increased. The production of p,p-BPA over o,p-BPA is also seen, especially as the WHSV goes below 5.

Example 5

As seen in FIGS. 3 and 4, there can be four different types of phenol: fresh phenol via feed line 200, tar cracking phenol via recycle line 264, treated tar cracking phenol via recycle line 274, and dry mother liquor mixed with tar cracking phenol via line 257. The effect of the quality of these different phenol types when used as feed on the selectivity of the reactor 210's formation of p,p-BPA was tested using a continuous lab reactor. Together with acetone and co-catalyst, the four phenol types were reacted and the effluent of the continuous lab reactor was analyzed to assess reaction selectivity. The selectivity was determined according to equation (1):

$$\text{Selectivity} = \frac{(p, p-BPA_{out} - p, p-BPA_{in})}{(p, p-BPA_{out} - p, p-BPA_{in}) + (impurities_{out} - impurities_{in})} * 100 \quad (1)$$

The treated tar cracking phenol was run through a cationic ion exchange resin having 8% crosslinkage. Results are shown in Table 3 below.

TABLE 3

|  | Fresh Phenol | Tar Cracking Phenol | Treated Tar Cracking Phenol | Mother Liquor + Tar Cracking Phenol |
|---|---|---|---|---|
| Selectivity (%) | 92.6 | 91.7 | 92.5 | 95.9 |
| Standard Deviation (%) | 0.7 | 0.8 | 0.6 | 1.5 |

As seen in the table, the selectivity of tar cracking phenol was the lowest. The selectivity of the treated tar cracking phenol was comparable to that of fresh phenol. The mother liquor plus tar cracking phenol stream represents the mixture normally recycled to the reactor (see FIG. 3, recycle line 257). The higher selectivity of this stream is generally due to the fact that the mother liquor contains a high amount of other reaction byproducts which can be reconverted to p,p-BPA by passing it through reactor 210 again.

Example 6

The catalyst activity is directly linked to the amount of p,p-BPA produced per unit of time per mass unit of catalyst used. Higher catalyst activity corresponds to a higher p,p-BPA production rate. The activity of the reactor catalyst, which is typically an acid catalyst, such as a sulfonated cationic ion exchange resin having 2% or 4% crosslinkage or a combination of such resins, decreases over time as a function of the total amount of p,p-BPA produced.

As discussed in Example 5, there can be four different types of phenol fed into the reactor 210. By running each type of phenol feed, mixed with acetone and co-catalyst, into a continuous lab reactor using a cationic ion exchange resin having 4% crosslinkage at a space velocity high enough to observe the p,p-BPA production rate decrease, the effect of the different types of phenol feed on the catalyst lifetime can be observed. Here, the WHSV was 40 hr$^{-1}$.

Figure 11:
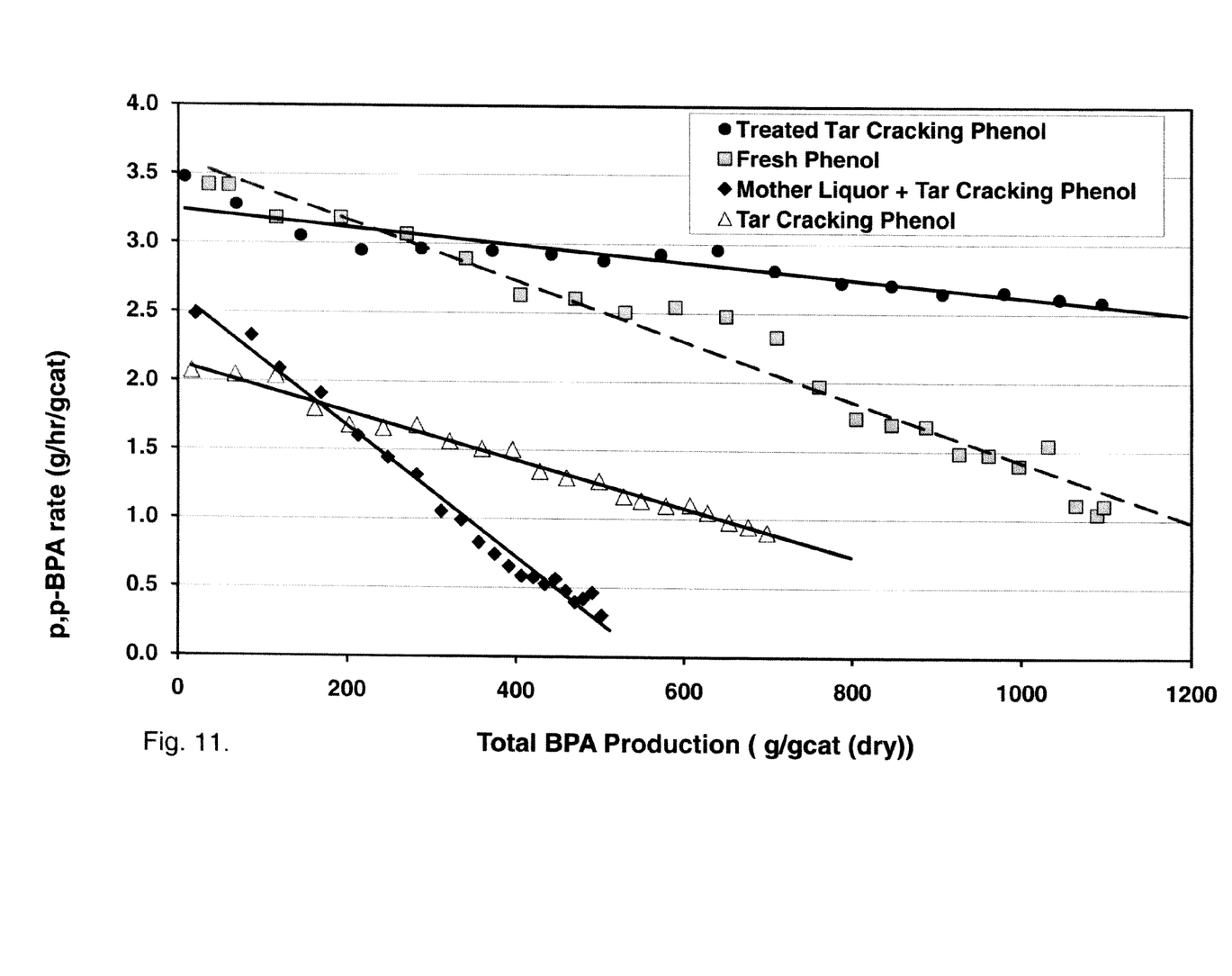
FIG. 11 is a graph showing the effect on catalyst lifetime of the methods of the present disclosure.

The results can be seen in FIG. 11. The treated tar cracking phenol provided the longest lifetime for the catalyst, even greater than the use of fresh phenol.

The methods of the present disclosure have been described with reference to exemplary embodiments. Obviously, modifications and alterations will occur to others upon reading and understanding the preceding detailed description. It is intended that the exemplary embodiments be construed as including all such modifications and alterations insofar as they come within the scope of the appended claims or the equivalents thereof.

We claim:

1. A process for producing 2,2-bis(4-hydroxyphenyl)propane (p,p-BPA), comprising:
   providing a liquid stream comprising phenol and 2,4,4-trimethyl-2-(4-hydroxyphenyl)chroman (chroman 1.5); and
   feeding the liquid stream to an acidic ion exchange resin at a temperature of from about 45° C. to about 100° C. to produce an effluent stream containing p,p-BPA, the acidic ion exchange resin having greater than 2% crosslinkage.

2. The process of claim 1, wherein the chroman 1.5 comprises from about 0.1 weight percent to about 6 weight percent of the liquid stream.

3. The process of claim 1, wherein the liquid stream further comprises a mercaptan selected from the group consisting of 3-mercaptopropionic acid, an ethene thiol, a propane thiol, an aliphatic thiol, and an aromatic thiol.

4. The process of claim 1, wherein the acidic ion exchange resin has from 6% to 10% crosslinkage.

5. The process of claim 1, wherein the acidic ion exchange resin is a resin selected from the group consisting of sulfonated styrenedivinylbenzene resins, sulfonated styrene resins, phenol formaldehyde sulfonic acid resins, and benzene formaldehyde sulfonic acid resins.

6. The process of claim 1, wherein the ion exchange resin contains sulfonic acid groups.

7. The process of claim 1, wherein the temperature is from about 53° C. to about 93° C.

8. The process of claim 1, wherein the temperature is from about 80° C. to about 95° C.

9. The process of claim 1, wherein the liquid stream in the ion exchange resin has a weight hourly space velocity WHSV, and the weight hourly space velocity WHSV of the liquid stream in the ion exchange resin is from 0 to about 20 hr$^{-1}$.

10. The process of claim 1, wherein the liquid stream in the ion exchange resin has a weight hourly space velocity WHSV, and the weight hourly space velocity WHSV of the liquid stream in the ion exchange resin is from about 0.5 hr$^{-1}$ to about 5 hr$^{-1}$.

11. The process of claim 1, wherein the effluent stream comprises from about 1 weight percent to about 12 weight percent of p,p-PBA.

12. A process for converting 2,4,4-trimethyl-2-(4-hydroxyphenyl)chroman (chroman 1.5) into 2,2-bis(4-hydroxyphenyl)propane (p,p-BPA), comprising:
    providing a liquid stream comprising phenol and chroman 1.5; and
    feeding the liquid stream to an acidic ion exchange resin at a temperature of from about 45° C. to about 100° C. to convert at least 50 weight percent of the chroman 1.5 to p,p-BPA.

13. The process of claim 12, wherein the chroman 1.5 comprises from about 0.1 weight percent to about 6 weight percent of the liquid stream.

14. The process of claim 12, wherein the acidic ion exchange resin has greater than 2% crosslinkage.

15. The process of claim 12, wherein the acidic ion exchange resin has 8% crosslinkage.

16. The process of claim 12, wherein the acidic ion exchange resin has 20% crosslinkage.

17. The process of claim 12, wherein the temperature is from about 53° C. to about 93° C.

18. The process of claim 12, wherein the liquid stream in the ion exchange resin has a weight hourly space velocity WHSV, and the weight hourly space velocity WHSV of the liquid stream in the ion exchange resin is from 0 to about 20 $hr^{-1}$.

19. The process of claim 12, wherein the liquid stream in the ion exchange resin has a weight hourly space velocity WHSV, and the weight hourly space velocity WHSV of the liquid stream in the ion exchange resin is from about 0.5 to about 5 $hr^{-1}$.

20. The process of claim 12, wherein at least 70 weight percent of the chroman 1.5 is converted to p,p-BPA.

21. The process of claim 12, wherein at least 90 weight percent of the chroman 1.5 is converted to p,p-BPA.

\* \* \* \* \*